(12) United States Patent
Taagaard et al.

(10) Patent No.: US 6,723,216 B2
(45) Date of Patent: Apr. 20, 2004

(54) METHOD AND APPARATUS FOR DETECTION OF A BUBBLE IN A LIQUID

(75) Inventors: Michael Taagaard, Hørsholm (DK); Allan Larsen, Bagsvaerd (DK)

(73) Assignee: Radiometer Medical A/S, Bronshoj (DK)

(*) Notice: Subject to any disclaimer, the term of this patent is extended or adjusted under 35 U.S.C. 154(b) by 0 days.

(21) Appl. No.: 10/134,914

(22) Filed: Apr. 29, 2002

(65) Prior Publication Data

US 2003/0080002 A1 May 1, 2003

Related U.S. Application Data

(63) Continuation of application No. PCT/DK00/00601, filed on Oct. 30, 2000.

(30) Foreign Application Priority Data

Oct. 29, 1999 (DK) .......................................... 1999 01546

(51) Int. Cl.[7] .............................................. G01N 27/404
(52) U.S. Cl. ...................... 204/401; 204/400; 204/408; 204/415; 205/775; 205/783
(58) Field of Search ................................. 204/401, 415, 204/408, 400; 205/782, 782.5, 783, 775

(56) References Cited

U.S. PATENT DOCUMENTS

| | | | |
|---|---|---|---|
| 3,997,420 A | * | 12/1976 | Buzza |
| 4,358,423 A | | 11/1982 | Nedetsky |
| 5,026,348 A | | 6/1991 | Venegas |
| 5,092,980 A | * | 3/1992 | Maurer et al. |
| 5,284,568 A | | 2/1994 | Pace et al. |
| 5,451,373 A | | 9/1995 | Lewis et al. |
| 5,631,552 A | | 5/1997 | Ogawa et al. |

FOREIGN PATENT DOCUMENTS

| | | |
|---|---|---|
| EP | 0 484 876 A1 | 5/1992 |
| WO | WO 96/41156 | 12/1996 |
| WO | WO 98/37402 | 8/1998 |

* cited by examiner

*Primary Examiner*—T. Tung
(74) *Attorney, Agent, or Firm*—Bryan Cave LLP; Maurice B. Stiefel

(57) ABSTRACT

A method for detection of a bubble in a liquid which is placed in a measuring chamber and is in contact with a sensor for measuring the partial pressure of a particular gas in a liquid is provided. The method includes performing a first measurement of the partial pressure of the particular gas in the liquid at a first pressure in the measuring chamber. Next, the pressure in the measuring chamber is changed to a second pressure. A second measurement of the partial pressure of the gas in the liquid at the second pressure in the measuring chamber is performed. An expected result of the second measurement based on the first measurement and assuming that no bubbles are present in the measuring chamber during any of the measurements is provided. The actual result of the second measurement is compared with the expected result and a conclusion is drawn on the presence of a gas bubble in the liquid based on the comparison. An apparatus for measuring the content of a particular gas in a liquid is also provided.

12 Claims, 3 Drawing Sheets

METHOD AND APPARATUS FOR DETECTION OF A BUBBLE IN A LIQUID

This is application is a continuation of international application PCT DK00/00601, filed Oct. 30, 2000.

The invention concerns a method for detection of a bubble in a liquid, which is placed in a measuring chamber and is in contact with a sensor for measuring the content of a particular gas in the liquid.

The invention also concerns an apparatus for measuring the content of a particular gas in a liquid and comprising a measuring chamber, a sensor connected to the measuring chamber for measuring the content of said gas in the liquid and for providing at least a first and a second measurement, and means for detecting a bubble in the liquid.

The invention is particularly suitable for use in connection with an apparatus for blood gas analysis but it can be used for detection of bubbles in any liquid placed in a chamber for which the partial pressure of a particular gas can be measured at two different pressures.

To be able to carry out a reliable measurement on a blood sample, one of the fundamental demands is that the measurement is performed under controlled conditions. Therefore a blood gas analysis apparatus is often equipped with a lot of self-monitoring equipment so that any error can be reported to the user of the apparatus. In blood measurement, a very serious source of error is bubbles in the blood sample, and particularly bubbles of atmospheric air, because these bubbles may affect the measuring result. If a blood sample contains a bubble, interchange of gasses will occur between the bubble and the blood. The content of e.g. $O_2$ or $CO_2$ in the blood may thus change, and a subsequent measurement will in such a case not reflect the real content of the gases in the blood sample. The problem is especially serious if a bubble is present in the measuring chamber itself, and measurement is performed on the bubble instead of on the blood sample.

In most blood gas analysis apparatuses, several liquid sensors are often placed in the sample channels of the apparatus. These liquid sensors monitor among others how far an introduced sample has travelled in the channels, and if there are any bubbles in the blood sample. In the prior art apparatuses, however, no actual monitoring takes place of whether any bubbles are present in the measuring chamber during the measurement, and therefore it is recommended that the user during measurement inspects the generally visible measuring chamber for the presence of bubbles.

U.S. Pat. No. 4,358,423 discloses a measuring apparatus for blood gas analysis comprising a capillary tube along which measuring and reference electrodes are placed. To detect any air bubbles in the capillary tube, the electrical resistance between preferably three points in the capillary tube is monitored two by two. These points may e.g. be one point in each end of the capillary tube and an intermediate point between the electrodes. The electrical resistances are measured between the intermediate point and each of the end points, respectively. Any presence of a bubble between the intermediate point and any of the end points will increase the resistance substantially. One of the points may be a reference electrode.

U.S. Pat. No. 5,631,552 discloses a method and an apparatus for detection of the presence of air bubbles in a liquid, mainly in blood in connection with dialysis, by monitoring the conductivity of the liquid.

U.S. Pat. No. 5,026,348 discloses a system for monitoring abnormalities in an intravenous catheter, for example air bubbles in the catheter, comprising a piezoelectric vibrator and a piezoelectric detector. The signal registered by the detector is compared with the input signal of the vibrator, and the result indicates the condition of the catheter.

U.S. Pat. No. 5,284,568 discloses a replaceable cartridge for an ion measuring apparatus comprising flow channels in which the air bubbles are detected by measuring the impedance between a bubble sensing element and a ground element.

WO 96/41156 discloses a device for controlling the flow of an intravenous fluid to a patient while monitoring whether there is any bubble in the liquid being delivered to the patient. The liquid runs through a diaphragm with a valve in each end. Bubbles are detected by exposing the diaphragm containing the liquid and with closed valves to a pressure change and then measuring by acoustic resonance any volume change of a measurement gas occupying a box in which the diaphragm is situated. Any volume change of the measurement gas indicates a volume change of the liquid in the diaphragm and thus whether any bubbles are present.

The object of the invention is to provide a method for detecting the presence of a bubble in a liquid in a measuring chamber.

A further object of the invention is to provide an apparatus for performing the method.

The object is achieved by a method which is characterized in performing a first measurement of the content of the particular gas in the liquid at a first pressure in the measuring chamber, changing the pressure in the measuring chamber to a second pressure, performing a second measurement of the content of said gas in the liquid at the second pressure in the measuring chamber, providing an expected result of the second measurement based on the first measurement and assuming that no bubbles are present in the measuring chamber during any of the measurements, and comparing the actual result of the second measurement with the expected result.

The invention is based on the realisation that liquids are substantially incompressible, while gas mixtures comply with Dalton's Law (the sum of partial pressures is equal to the total pressure).

A gas sensor generally measures the equilibrium partial pressure of the particular gas at the interface between the sensor and the sample phase (gas or liquid) in the measuring chamber. Thus, if a bubble is located near the sensor then the partial pressure of said gas in the bubble may influence the sensor response and consequently the measuring result. If on the other hand only liquid is present near the sensor then an equilibrium partial pressure of said gas in the liquid will determine the sensor response and consequently the measuring result.

The equilibrium partial pressure of the particular gas in the liquid will not be affected by a change of the total pressure in the measuring chamber as the liquid is incompressible. Consequently, if no bubble is present near the sensor, then the partial pressure of said gas at the interface between the sensor and the liquid will not change. In contrast, the partial pressure of a gas, i.e. in a bubble, will be affected by a change of the total pressure in the measuring chamber in accordance with Dalton's Law. The presence of a bubble near the sensor will accordingly cause a change of the partial pressure of said gas at the interface between the sensor and the fluid. Thus, if the fluid in the measuring chamber is exposed to a pressure change then a comparison of a first measurement before the pressure change and a second measurement after the pressure change will indicate whether a bubble has been present during the measurement.

In reality, a gas phase will always be present above a liquid phase. This gas phase may be located outside the measuring chamber. When a positive pressure is established, gas from the gas phase will diffuse through the phase boundary and into the liquid and increase the equilibrium partial pressure of the gas in the liquid. However, this diffusion is a relatively slow process compared to the time it takes to provide a superimposed pressure change.

This diffusion of gas from the gas phase to the liquid phase will therefore (if no bubble is present) not affect the measurement in the measuring chamber unless a gas sensor with a very long response time is used. The detection of the presence of a bubble in the measuring chamber is thus based on the transient response to a pressure change.

A bubble being present during the first measurement may be forced out of the chamber due to the pressure change before an increased partial pressure can be detected by the sensor during the second measurement. Also in this case the sensor response will change significantly since suddenly the equilibrium partial pressure of the gas in the liquid will be measured by the sensor. A bubble may for instance be forced out of the measuring chamber if a sample channel runs through the measuring chamber and the pressure change is applied from one side of the chamber.

The herein described bubble detection principle can be used to detect bubbles in many types of apparatuses. The only demands are that the sensor/electrode for the particular gas is exposed to sufficiently controlled conditions and that it must be possible to establish a positive pressure or a negative pressure in the measuring chamber of said sensor/electrode. The sensor may thus be based on any measuring principle, such as electrochemical or optical.

An electrochemical oxygen sensor usually measures a flux of oxygen through a gas permeable membrane which is related to the partial pressure of oxygen at the interface between the sensor and sample phase in the measuring chamber. An electrochemical carbon dioxide sensor usually measures an equilibrium concentration of bicarbonate in a sensor solution which is related to the partial pressure of carbon dioxide at said interface.

Optical gas sensors usually measures an effect of said gas, such as absorbance or quenching of luminescence, which is related to the partial pressure of said gas at the interface between the membrane and the sample phase in the measuring chamber. The membrane in such sensors may be a coating of a luminophor on the wall of the measuring chamber.

In the above method the gas to be sensed may for instance be oxygen, carbon dioxide or ammonia, but any gas in a liquid may be measured. A gas sensor may also be provided in a measuring chamber for other analytes with the sole purpose of detecting the presence of bubbles.

The first measurement may be just one or two distinct measurements but is usually performed over a certain measuring period. The measurements may comprise several distinct measurements within the measuring period mentioned or a continuous monitoring within said measuring period. If the first measurement is performed over a measuring period then this may be used to give some information about the response time of the sensor.

The second measurement may also be just a few distinct measurements or be performed over a certain measuring period.

To provide the expected result it is assumed that no bubbles are present. Since liquid is incompressible as mentioned above the expected result will be a continuous course of the sensor signal and the first measurement may provide an estimation for the response signal during the second measurement.

If the first measurement lasts for such a long time that complete equilibrium is obtained, then after a pressure change no substantial change in slope or level will occur, and the expected result will be equal to the parameter in question (slope or level) before the pressure change. If no equilibrium has been obtained during the first measurement, then the expected result may be estimated by means of a curve fit on the basis of previous experience as to the course of the measuring curve. The curve fit may for instance be an approximation to a straight line, a polynomial, an exponential function etc. Finally, it is conceivable to estimate the expected result by multivariable analysis/calibration on the basis of response parameters and sensor parameters.

The comparison criterion for comparing the second measurement with the expected result may for instance be a maximum acceptable deviation from the expected result, for instance a parameter for a curve, such as a slope or a level, or an approximated curve sequence.

The parameter may be expressed by a measured pressure, a measured current from the sensor or another similar expression as is known per se.

The pressure change can be constituted by either positive pressure or negative pressure. The pressure change must have a size which is sufficient to obtain, when a bubble is present in the chamber, a detectable change of response in consequence of the pressure change. The pressure change may e.g. be in the range of 5–100%. It is preferred that the pressure change is in the range of 10–30%. The pressure change is preferably constituted by positive pressure as this is easier to create. The pressure change should not be so big that it causes damage to the sensors. However, the greater a pressure change the greater a deviation from the expected result is observed if a bubble is present.

If a pressure change results in a change of the sensor response, even though no bubble is present, then the estimation of the expected result should compensate for this.

The further object is achieved by an apparatus, which is characterized in that the means for detecting the bubble in the liquid comprise means for changing the pressure in the measuring chamber, means for providing an expected result of the second measurement based on the first measurement and assuming that no bubbles are present in the measuring chamber during any of the measurements, and means for comparing an actual result of the second measurement with the expected result.

The apparatus mentioned may be a blood gas analysis apparatus.

Detection of bubbles is preferably performed in the measuring chambers of the blood gas analysis apparatus in which the content of $O_2$ or $CO_2$ in the sample are determined.

The herein described bubble detection principle is however not limited to blood gas analysis apparatuses, but can also be used in other types of apparatuses. The only demands are that the sensor/electrode for the particular gas is exposed to sufficiently controlled conditions and that it must be possible to establish a positive pressure or a negative pressure in the measuring chamber of said sensor/electrode.

It has been found that there are certain demands to the time constant $\tau$, i.e. the response time of the sensor, in the system. If $\tau$ is too high, the slope of the response curve becomes too small for the system to become stable within the relevant measuring time, and, as previously mentioned, substantial diffusion of gas from the bubble to the liquid may occur. If $\tau$ is too low, the system reacts so fast that equilibrium will be obtained almost instantly and the detection of changes of the slope is very complicated.

BRIEF DESCRIPTION OF THE DRAWINGS

In the following, the invention is further described by means of examples in which the method is applied to a measuring chamber for measuring oxygen in an apparatus for blood gas analysis and with reference to the drawing in which

FIG. 1 illustrates the wet section of a blood gas analysis apparatus of the applicant's ABL™700 series. The apparatus is equipped with a sample inlet 1, analysis modules 2, 3 and 4 comprising measuring chambers for measurement of, respectively, pH and blood gases, electrolytes and metabolites, and oximetry parameters. The measuring principles for these sensors may e.g. be as described in Tietz N W, Pruden E L, Siggaard-Andersen O. Electrolytes, Blood Gases, and Acid-Base Balance. In: Tietz N W, ed. Fundamentals of Clinical Chemistry. Philadelphia: W. B. Saunders Company, 1987: 614–668. The analysis modules 2, 3, 4 are placed in a non-illustrated thermostatic block so that analyses can be performed at a well-defined temperature. The apparatus also comprises pumps 5a–5d and various channels to transport samples, cleaning solutions, calibration solutions and quality control solutions round in the apparatus. It is further equipped with a cleaning solution container 6, a waste container 7, calibration and cleaning solution containers 8 and flush gas containers 9. The liquid sensors 10a and 10b monitor the flow of liquid in the apparatus. The valves 11 are used for blocking the channels. The pH/blood gas analysis module 2 (see especially FIGS. 2–4) is equipped with one of the liquid sensors 10a, measuring chambers including a $pO_2$- and a $pCO_2$-measuring chamber 12 and 13 respectively, and one of the liquid sensors 10b.

Figure 1:
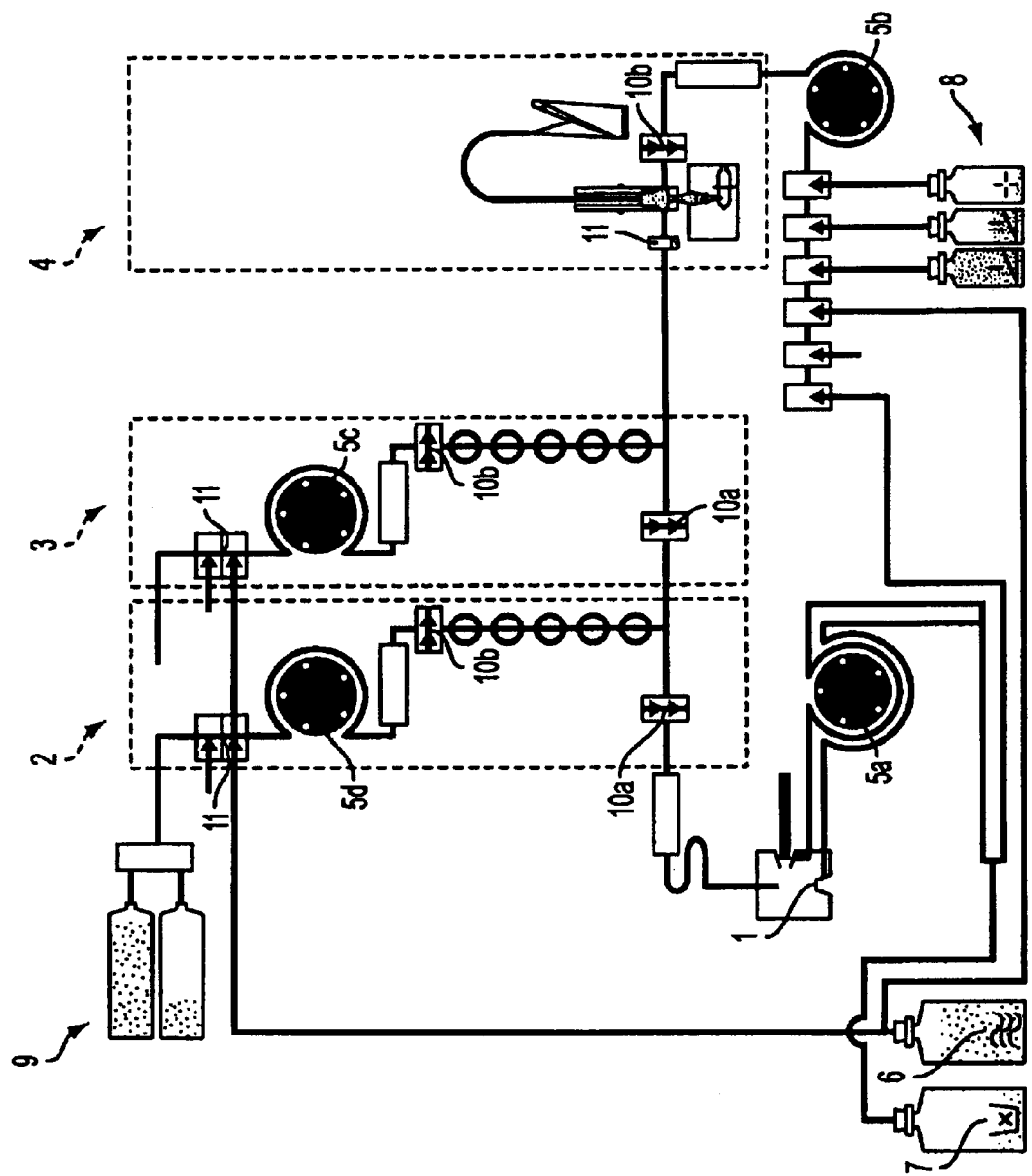
FIG. 1 illustrates the wet section of a prior art blood gas analysis apparatus.

When a blood sample is analysed, it is introduced into the apparatus by means of the pumps 5a–d. The liquid sensors 10a monitor if there are any larger bubbles in the sample i.e. bubbles extending across the entire cross-section of the sample channel. When the sample reaches the liquid sensors 10b, these signal to stop the feeding of the sample, so that the blood sample is kept within certain parts of the apparatus. When the measurements in the measuring chambers are finished, the blood sample is conducted out of the measuring chambers and is led to the waste container 7. This is followed by a cleaning procedure, first with cleaning solution and then with flush gas, after which the apparatus is ready for the next sample. At intervals, various control procedures are also carried out to ensure that the apparatus works properly and is calibrated correctly.

As described above, the apparatus and its application are known per se.

A source of serious errors is if bubbles of e.g. atmospheric air or flush gas are present in the blood sample as this may cause noise in the measurements, the impedance in the measurements may rise, and this may affect the transient response of the sensors. The error is especially serious if a bubble is located in the $pO_2$- or $pCO_2$-measuring chambers 12 or 13, so that measurements of the partial pressures of $O_2$ and $CO_2$ in the bubble take place in stead of measurement of the partial pressures of $O_2$ and $CO_2$ in the sample.

When a sample is introduced into the apparatus, the liquid sensors 10a will monitor, as mentioned above, if there are any larger bubbles in the sample. Smaller bubbles located inside the sample cannot be detected by these sensors. Further, during filling, a constriction of atmospheric air or flush gas may occur in a measuring chamber, if the sample does not flow and spread smoothly in the measuring chambers, or it may occur that micro bubbles in the sample accumulate into a larger bubble. None of these types of bubbles will be detected by the liquid sensors 10a.

Presence of such smaller or constricted bubbles in a measuring chamber can however be detected by means of the method according to the invention. An embodiment of the method will be described below applied to the $pO_2$-measuring chamber 12, to which an oxygen sensor is connected for measurement of the partial pressure of $O_2$ in the sample.

A blood sample is introduced into the apparatus at the inlet 1. By means of the pumps 5a–b, the sample is led to the measuring chambers in the analysis modules 2, 3 and 4. Then a usual measurement is carried out. The measuring response of the oxygen sensor in the $pO_2$-measuring chamber is continuously registered for approx. 30 seconds (the measuring period from t=0 to the vertical line a on FIG. 5). Then a pause is made for approx. 6 seconds, while other measurements in the apparatus are finished. Subsequently the inlet 1 is closed and is thus completely tight towards the surroundings. The pressure in the measuring chambers is increased approx. 10–30% by means of the pump 5b. The other pumps do not move, so that the blood sample is pressure-tightly captured inside the channels and measuring chambers of the apparatus between the pumps 5a–d. Approx. a couple of seconds (at the vertical line b in FIG. 5) after the increase of pressure has been applied, the registration of the measuring response of the oxygen sensor is resumed, and the registration is continued until approx. 45 seconds or more have passed from when the blood sample was introduced into the apparatus.

Figure 2:
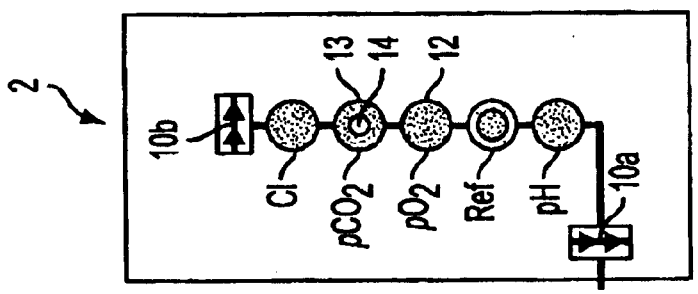
FIG. 2 illustrates an enlarged section of FIG. 1 showing the pH and blood gas analysis module.
Figure 5:
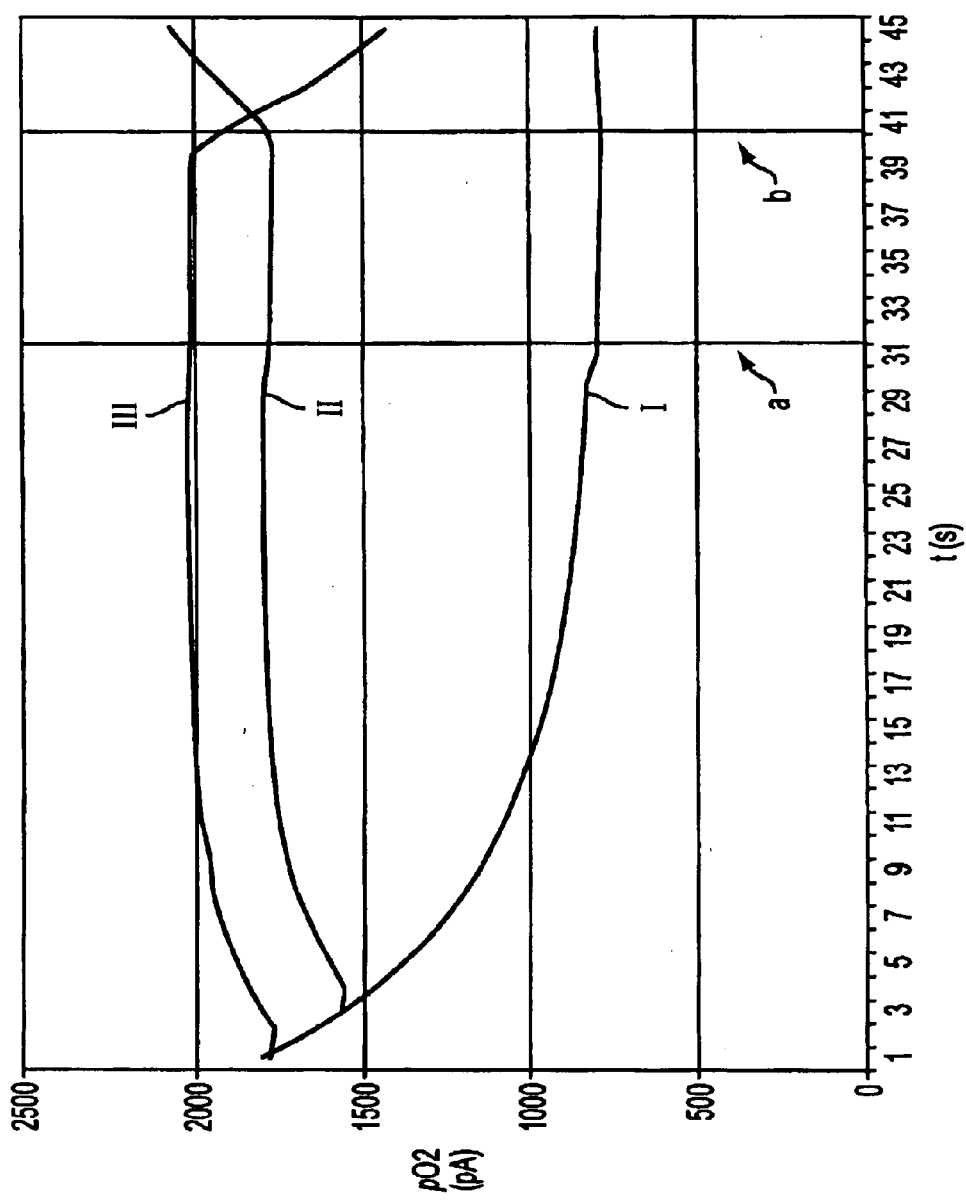
FIG. 5 illustrates curves representing the response when measuring on liquids with and without bubbles in the measuring chamber.

In FIG. 2 an analysis module 2 is illustrated during measurement of a blood sample without bubbles. The corresponding measuring response series for the oxygen sensor is represented by curve I in FIG. 5. As illustrated in FIG. 5, the first measurement has lasted for such a long time (until the vertical line a) that almost total equilibrium has been obtained. The curve hardly changes during and after the increase of pressure indicating that no bubble is present in the measuring chamber.

Figure 3A:
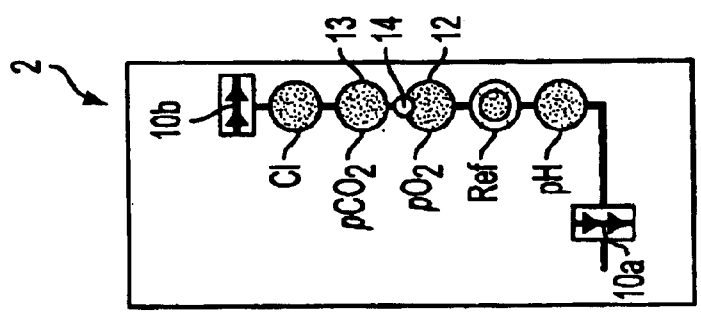
FIGS. 3a, 3b, 4a and 4b illustrate the same as FIG. 2 but with a bubble in various situations.
Figure 3B:
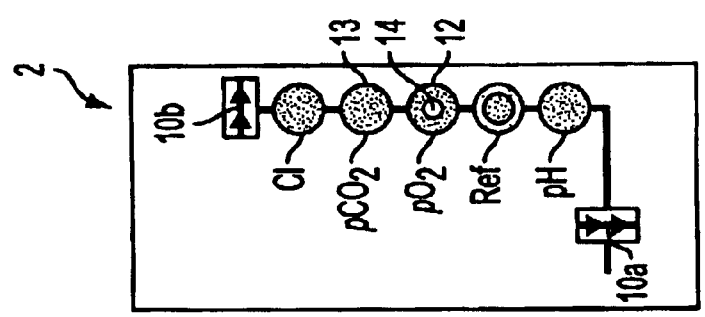

FIG. 3a illustrates an occurrence where a bubble 14 is present in the $pO_2$-measuring chamber 12 during the normal measurement. During the increase of pressure, the bubble 14 remains in the $pO_2$-measuring chamber 12 as shown in FIG. 3b. The curve II in FIG. 5 represents a measuring response series for this occurrence. It can be seen that the measuring values and thus also the curve II rise significantly after the increase of pressure. As described earlier this is due to the fact that the partial pressure in the bubble increases with the total pressure.

Figure 4A:
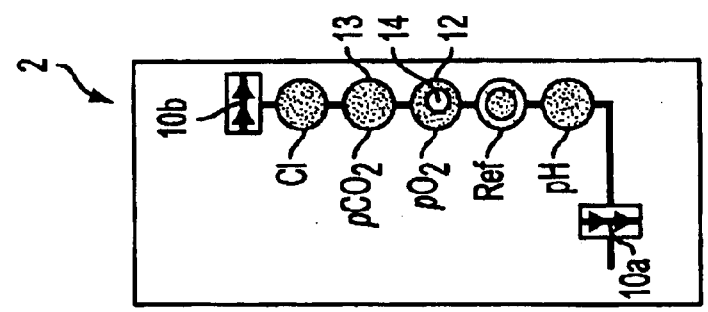

FIG. 4a illustrates another occurrence in which there is a bubble 14 in the $pO_2$-measuring chamber 12 during the normal measurement. At the increase of pressure (FIG. 4b) the bubble 14 is forced out of the $pO_2$-measuring chamber 12 and into the $pCO_2$-measuring chamber 13. The curve III in FIG. 5 represents a measuring response series for this occurrence. It is noted that the measuring values and thus also the curve III drops significantly after the increase of pressure, i.e. after the bubble has disappeared from the pO$_2$-measuring chamber. This is due to the fact that the partial pressure of O$_2$ in the bubble was significantly higher than in the blood sample.

Figure 4B:
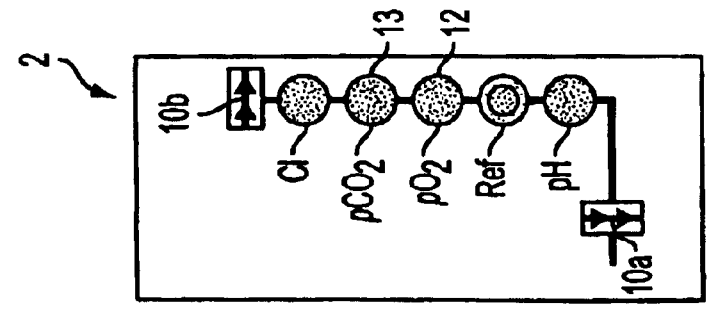

The course of the curves II and III may be obtained from various situations. Besides the situation mentioned in connection with FIGS. 3a–b, a course of the curve, as illustrated by curve II in FIG. 5, may be obtained in case a bubble is forced out during the increase of pressure, as illustrated in FIGS. 4a–b, having a partial pressure of O$_2$ in the bubble, which is lower than in the blood sample. The course of the curve II may also be obtained from a situation where a bubble with a partial pressure of O$_2$ being higher than in the blood sample is forced from an adjoining measuring chamber and into the pO$_2$-measuring chamber during the increase of pressure.

Various criteria may be used to establish whether according to the course of the registered measuring response a bubble has been present in the pO$_2$-measuring chamber during the first and/or the second measurement, in which cases the measuring result has to be rejected.

One criterion is a comparison of the level of the measuring response before the increase of pressure and at the end of the registration period after the increase of pressure. A significant change of the level indicates that a bubble has been present during either both or one of the measurements.

Another criterion is to compare the slope of the curve for the measuring response series before and after the increase of pressure. A significant change of the slope indicates that a bubble has been present during either both or one of the measurements.

A third criterion is based on curve fitting. Various functions may be fitted to the data obtained for the first measurement. The deviation from this estimated curve of the measuring points during the second measurement may be evaluated, for instance by sum of squares deviation.

As mentioned above, other advanced criteria may be used.

In the following example a response model for an oxygen sensor suitable for use in the above-described ABL™700 series is demonstrated. Curve fitting has been chosen to estimate the expected result since this alternative is fairly simple to apply and yet very reliable. Also, the time constant $\tau$ of the sensor may be determined from such a curve fit. Further, the acceptable limits for the time constant $\tau$ of the sensor used in the method are estimated for said system (oxygen sensor measuring on blood) as well as criterions of approval/rejection of the measuring result.

The partial pressure of O$_2$ is calculated for the individual measurements from the sensor current in a usual way (see e.g. the above referenced Tietz).

It has been found that the obtained measuring response series may be approximated by the following exponential response model:

$$p(t)=p_s+(p_0-p_s)\exp(-t/\tau) \qquad (1)$$

wherein p(t) is the measured value of the partial pressure at time t, p$_0$ is the initial value of the partial pressure of the sample (at time=0), p$_s$ is the true value of the partial pressure of the sample (at time→∞) and $\tau$ is the time constant for the sensor.

In order to apply the model p$_0$ and $\tau$ must be determined.

$\underline{\tau}$

The value of $\tau$ for the oxygen sensor used is estimated from the following equation 2:

$$\tau=-12 \text{ sec.}/\ln([p(30)-p(18)]/[p(18)-p(6)]) \qquad (2)$$

The points are selected to cover the greater part of the transient response. In this case for instance p(6), p(18) and p(30) (see curve I of FIG. 5). $\tau$ is preferably estimated every time the apparatus is calibrated, but the estimation may be performed more or less often.

$\underline{p_0}$ p$_0$ is in this example the known partial pressure of oxygen in the flush gas which is 140 mmHg.

$\underline{p_s}$

Each time an oxygen measurement is performed p$_s$ is estimated from the following equation 3:

$$p_s[p(6)p(30)-p(18)^2]/[p(6)+p(30)-2p(18)] \qquad (3)$$

The points are taken from the first measurement and selected to cover the greater part of the transient response. In this case for instance p(6), p(18) and p(30) (see curve I of FIG. 5).

With p$_s$ inserted in equation 1 and using the above values for p$_0$ and $\tau$ an expected level, slope or curve sequence may be obtained. The second measurement may be compared with this level, slope or curve sequence.

Some criterions of approval/rejection of a measurement are evaluated below. Thus, for a pressure change constituted by an increase of pressure of approx. 30% a level difference of +/−5% was used and/or a change of the slope of the curve of +/−1.5 mmHg/sec., so that the measurement was approved if it was within the limits.

If approved, then the above calculated p$_s$ is accepted as the measured partial pressure of oxygen in the sample.

Estimation of Some Approval/Rejection Criteria

In order to select appropriate criteria of approval/rejection of the measuring result, models are set up to describe the deviation of the second measurement from the expected result as a function of p$_s$ that may be observed if a bubble is present near the sensor.

In the apparatus used a stability criterion for the first measurement of oxygen exists which is given by:

$$[p(30)-p(18)]/[p(18)-p(6)]<0,6 \qquad (4)$$

This implicates that the maximum value of the time constant is $\tau<24$ seconds. The minimum value of $\tau$ is determined by limitations in the construction of sensors. The minimum value is thus $\tau=3$. Experiments showed that $\tau$ in the systems used was often about 11 s.

For the above lower and the higher limit of $\tau$ the expected result of the second measurement if no bubble is present near the sensor as a function of p$_s$ may estimated as described above, only using $\tau=3$ or $\tau=24$, respectively.

To model the result of the second measurement that may be observed upon an increase of pressure of approximately 30% if a bubble is present near the sensor as a function of p$_s$, the response model of equation 1 may also be used. Only in this case p$_0$ is the partial pressure measured at the time of the increase of pressure and the new p$_s$ is according to Dalton's Law equal to 1,3 times the p$_s$ observed if no bubble is present.

In the relevant measuring interval for p$_s$ the deviation of the second measurement if a bubble is present from the expected result of the second measurement if no bubble is present may be plotted as a function of p$_s$.

If a percentage difference of level with and without a bubble approximately 5 sec. after the pressure change is plotted against p$_s$ an acceptable criterion of approval/rejection of a measurement is a level difference of +/−5%. If a difference of slope with and without a bubble approximately 5 sec. after the pressure change is plotted against p$_s$ an acceptable criterion of approval/rejection of a measurement is an average change of slope of the curve of +/−1.5 mmHg/sec. The measurements are thus approved if they are within the limits.

The lower limits of the criterions were included to detect occurrences where a bubble being situated in the measuring chamber during the first measurement was replaced by liquid with a lower partial pressure during the increase of pressure (the bubble was forced out of the measuring chamber), or where a bubble with a partial pressure of $O_2$, which was lower than in the blood sample, was forced from an adjoining measuring chamber into the $pO_2$-measuring chamber during the increase of pressure. These occurrences will show a course of the measuring response similar to curve III in FIG. 5.

The choice of the above response model is based on the oxygen sensor employed. Other models adjusted to the chosen measuring sensor may be employed with corresponding comparison criterions. For other gas sensors and sample liquids the response models, limits of $\tau$ and comparison criterions may be evaluated in a similar way.

The detection method according to the invention is based on establishment of a difference in pressure. It is therefore important to ensure that the apparatus is sufficiently pressure-tight, so that the wanted difference in pressure can actually be established and maintained during the measurements.

In the experiments it was found that approx. 95% of all bubbles were detected with the method according to the invention, and that the occurrences in which a bubble was detected, without the actual presence of a bubble, was close to 0. In most occurrences where the method did not detect a presence of a bubble, the partial pressure of $O_2$ in the bubble was very close to the partial pressure Of $O_2$ in the sample. No lack of detection of the presence of bubbles was observed when there was a significant difference between the partial pressure of $O_2$ in the bubble and the partial pressure of $O_2$ in the blood sample.

What is claimed is:

1. A method for detection of a bubble in a liquid which is placed in a measuring chamber and is in contact with a sensor for measuring the partial pressure of a particular gas in the liquid characterized in
    (a) performing a first measurement of the partial pressure of the particular gas in the liquid at a first pressure in the measuring chamber,
    (b) changing the pressure in the measuring chamber to a second pressure,
    (c) performing a second measurement of the partial pressure of said gas in the liquid at the second pressure in the measuring chamber,
    (d) providing an expected result of the second measurement based on the first measurement and assuming that no bubbles are present in the measuring chamber during any of the measurements, and
    (e) comparing the actual result of the second measurement with the expected result and drawing a conclusion on the presence of a gas bubble in the liquid based on said comparison.

2. The method according to claim 1, characterized in that at least the first measurement is performed over a certain measuring period.

3. The method according to claim 1, characterized in that the expected result is a parameter of a measurement curve representing the signal from the gas measuring sensor during the first measurement.

4. The method according to claim 3, characterized in that the parameter is a slope of the measurement curve.

5. The method according to claim 3, characterized in that the parameter is a level of the measurement curve.

6. The method according to claim 1, characterized in that the expected result is estimated by means of a curve fit on a measurement curve representing the signal from the gas measuring sensor during the first measurement.

7. The method according to claim 1, characterized in that at least the first measurement comprises several distinct measurements performed over the measuring period or a continuous monitoring over said measuring period.

8. The method according to claim 1, characterized in that the pressure change between the first and the second measurement is in the range of 5%–100%.

9. The method according to claim 8, characterized in that the pressure change between the first and the second measurement is in the range of 10%–30%.

10. An apparatus for measuring the content of a particular gas in a liquid comprising a measuring chamber, a sensor connected to the measuring chamber for measuring the partial pressure of said gas in the liquid and for providing at least a first and a second measurement, and means for detecting a bubble in the liquid, characterized in that the means for detecting the bubble in the liquid comprises:
    (a) means for changing the pressure in the measuring chamber,
    (b) means for providing an expected result of the second measurement based on the first measurement and assuming that no bubbles are present in the measuring chamber during any of the measurements, and
    (c) means for comparing an actual result of the second measurement with the expected result.

11. The apparatus according to claim 10, characterized in that the apparatus is an apparatus for blood gas analysis.

12. The apparatus according to claim 10, characterized in that the sensor for measurement of the content of a particular gas in the measuring chamber comprises a $pO_2$-electrode or a $pCO_2$-electrode.

* * * * *